United States Patent [19]

Liu et al.

[11] Patent Number: 4,686,299
[45] Date of Patent: Aug. 11, 1987

[54] AEROCAVIN ANTIBIOTICS

[75] Inventors: Wen-Chih Liu, Princeton Junction; William L. Parker, Pennington; Pushpa Singh, Piscataway; Richard B. Sykes, Belle Mead, all of N.J.

[73] Assignee: E. R. Squibb & Sons, Inc., Princeton, N.J.

[21] Appl. No.: 885,983

[22] Filed: Jul. 14, 1986

Related U.S. Application Data

[63] Continuation-in-part of Ser. No. 827,857, Feb. 10, 1986.

[51] Int. Cl.$^4$ .................................. C07D 313/00
[52] U.S. Cl. ............................ 549/271; 549/550; 435/117; 514/450
[58] Field of Search ........................ 549/271

[56] References Cited

PUBLICATIONS

Antibiotics: Origin, Nature & Properties, T. Korzybski et al. (1978), American Society for Microbiology, Washington, DC, pp. 131-132.
M. Nobuhara et al, Chem. Pharm. Bull., vol. 24, pp. 832-834 (1976).

Primary Examiner—Norma S. Milestone
Attorney, Agent, or Firm—Lawrence S. Levinson; Donald J. Barrack

[57] ABSTRACT

Aerocavin, a novel antibiotic substance having the structure

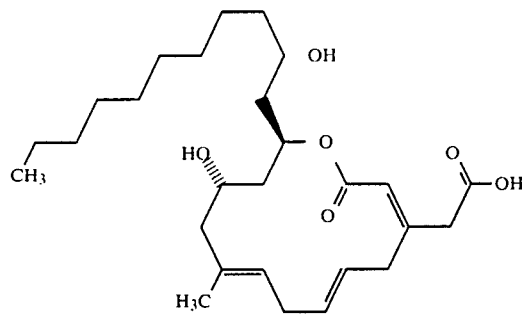

and aerocyanidin, a novel antibiotic substance having the structure

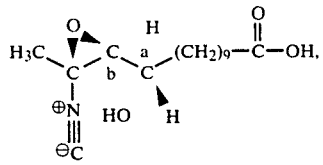

can be prepared by cultivation of the microorganism *Aerocavin caviae* SC 14,030 A.T.C.C. No. 53434.

1 Claim, No Drawings

AEROCAVIN ANTIBIOTICS

This application is a continuation-in-part of copending U.S. patent application Ser. No. 827,857, filed Feb. 10, 1986.

Cultivation of a strain of the microorganism *Aeromonas caviae* SC 14,030, which has been deposited in the American Type Culture Collection as A.T.C.C. No. 53434, yields a mixture of antibiotic substances. The components of the mixture have been separated and designated aerocavin and aerocyanidin. Each component has activity against gram positive organisms.

The chemical structure of aerocavin has been analyzed and found to be:

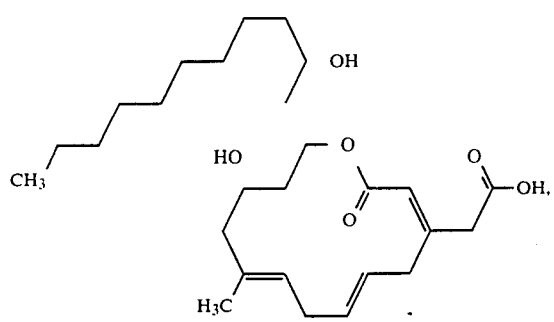

i.e., [3E,6E,9E,12α, 14β(R*)]-12-hydroxy-14-(2-hydroxyundecyl)-10-methyl-2-oxooxacyclotetradeca-3,6,9-triene-4-acetic acid. The asterisk in the above name indicates that the 2-position of the hydroxyundecyl side-chain has the same chirality as the hydroxy group at the 12-position of the nucleus. The other two assymmetric centers are in the correct relative configuration with respect to that center. The compound is distinguished from its enantiomer by its optical rotation which is about $[\alpha]_D^{22} = +25.1°$ (c=0.9, methanol).

The chemical structure of aerocyanidin has been found to be

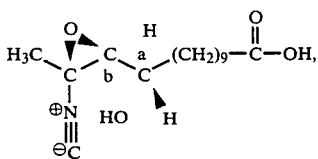

i.e., [2α(R*),3α]-k-hydroxy-3-isocyano-3-methyloxiraneundecanoic acid. The asterisk in the above name indicates that the chirality at the carbon atoms labeled "a" and "b" in the above structural formula is the same. The absolute configuration is not known, but aerocyanidin is distinguished from its enantiomer by its optical rotation which is about $[\alpha]_D^{23} = -20°$ (c=0.5, methanol).

DETAILED DESCRIPTION OF THE INVENTION

The Microorganism

The microorganism used for the production of aerocavin and aerocyanidin is *Aeromonas caviae* SC 14,030. A subculture of the microorganism can be obtained from the permanent collection of the American Type Culture Collection, Rockville, Md. Its accession number in the repository is A.T.C.C. No. 53434. In addition to the specific microorganism described and characterized herein, it should be understood that mutants of the microorganism (e.g., mutants produced through the use of X-rays, ultraviolet radiation, nitrogen mustards, etc.) can also be cultivated to produce aerocavin and aerocyanidin.

Isolation of *Aeromonas caviae* SC 14,030 from a water sample (in this instance obtained in Allamuchy Mountain State Park, New Jersey) in which it is present can be accomplished by plating the sample onto an agar of the following composition:

| | |
|---|---|
| Tryptone | 10.0 g |
| Glucose | 5.0 g |
| Bile salts #3 (Difco Laboratories) | 1.5 g |
| Agar | 15.0 g |
| Distilled water to | 1,000 ml |
| Cycloheximide (1% aqueous solution)* | 10.0 ml |

*Filter sterilized and added to the medium that has already been adjusted to pH about 6.7 and sterilized by autoclaving at 121° C. for 30 minutes.

After 48-72 hours incubation at about 25° C., the colonies of *Aeromonas caviae* SC 14,030 are isolated from the plated sample. The isolated colonies are picked off onto an agar medium composed of:

| | |
|---|---|
| Yeast extract | 5.0 g |
| Glucose | 5.0 g |
| MgSO$_4$.7H$_2$O | 0.1 g |
| FeSO$_4$.7H$_2$O | 0.1 g |
| Soil extract filtrate* | 200.0 ml |
| Agar | 17.5 g |
| Tap water | 800.0 ml |

*Soil extract filtrate is made by bringing to a boil a suspension of soil in tap water (1:2, v/v) and then allowing to simmer for about 60 minutes. After cooling, the extract is filtered through cheesecloth, then centrifuged to remove most of the remaining solids and finally filtered through Whatman 4 filter paper. The resulting liquid is sterilized by autoclaving at 121° C. for 20 minutes.

The medium is sterilized in an autoclave at 121° C. for 30 minutes.

*Aeromonas caviae* SC 14,030 is a gram negative rod, motile by means of monotrichous, polar flagella. Lateral to sub-polar flagella are occasionally seen. The organism is cytochrome oxidase positive and metabolizes glucose fermentatively without production of gas. It is resistant to the vibrostat 2,4-diamino-6,7-diisopropylpteridine and is DN-ase positive. These characteristics place the organism in the genus Aeromonas.

The culture, *Aeromonas caviae*, SC 14,030, matches the description of *Aeromonas caviae* in those key characteristics that serve to differentiate this species from *Aeromonas hydrophilia* and *Aeromonas sobria*, the two other members of this genus that are motile, i.e., being positive for esculin hydrolysis and for 1-arabinose utilization. Acetoin production, production of gas from glucose and production of hydrogen sulfide from cysteine are all negative. *Aeromonas caviae*, SC 14,030 is, therefore, identical to *Aeromonas caviae* and is so identified, in accordance with the description of *Aeromonas caviae* by M. Popoff (Bergey's Manual of Systematic Bacteriology, Vol. 1. Eds. N. R. Krieg and J. G. Holt, Williams and Wilkins, Baltimore, Md., pgs. 546-547, 1984).

The Antibiotics

The antibiotics aerocavin and aerocyanidin can be produced by cultivating *Aeromonas caviae* A.T.C.C. No. 53434 at, or about, room temperature (25° C.) under submerged aerobic conditions in an aqueous nutrient medium containing an assimilable source of carbon and an assimilable source of nitrogen. The fermentation is carried out until substantial antibiotic activity is imparted to the medium, usually about 18 to 48 hours, preferably about 24 hours.

The isolation procedure can be monitored by conventional means of paper disc-agar diffusion assay using, for example, *Staphylococcus aureus* FDA 209P. Additionally, aerocyanidin can be monitored colorimetrically by the Sievert-Hermsdorf method (P.A.S. Smith, "The Chemistry of Open-Chain Organic Nitrogen Compounds", Benjamin, N.Y., 1965; Vol. 1, p. 225) which gives a blue color with isocyanides. Samples to be tested, 0.1 ml, can be added to 0.9 ml of a reagent prepared by mixing equal portions of a 1 mg/ml solution of 3,3',5,5'-tetramethybenzidine in methanol:acetic acid, 9:1, v/v and a 3 mg/ml solution of cupric acetate monohydrate in water. The increase in absorption at 370 nm relative to a blank prepared from ethanol and the reagent is proportional to the quantity of aerocyanidin present.

Aerocavin can be separated from the fermentation medium and purified using art-recognized techniques. For example, the broth can be centrifuged to remove the cells of the producing microorganism. The supernate, adjusted to a pH of about 5 with an acid (e.g., hydrochloric acid) can be extracted with ethyl acetate, and the extract concentrated in vacuo to a syrup.

The syrup can be chromatographed on a column of silicic acid with solvents, e.g., hexane-chloroform, chloroform and finally, chloroform-methanol. The bioactive fractions, detected by conventional means of paper disc-agar diffusion assay against *Staphylococcus aureus* or *Staphylococcus epidermidis*, can be combined, concentrated in vacuo, and the residue chromatographed on a Sephadex LH-20* column prepared and subsequently eluted with a solvent mixture of chloroform: methanol:-heptane, 1:3:6 (v/v/v). Active fractions can be pooled, concentrated in vacuo, and further purified by chromatography on cellulose with heptane and heptane-ether. Rechromatography of the pooled, active fractions on cellulose affords highly purified aerocavin that crystallizes after concentration of the active eluate.

*Sephadex LH-20: alkylated crosslinked dextran gel beads, Pharmacia Fine Chemicals, AB, Uppsala, Sweden.

An alternative technique for separating aerocavin from the fermentation medium, and one which yields aerocyanidin as well as aerocavin, comprises first adjusting the pH of the fermentation broth to 6 and centrifuging to remove cells and other particulate matter. The clear supernate can be extracted with ethyl acetate and the resulting organic layer, containing the antibiotic activity, can be concentrated in vacuo to a residue that can then be subjected to distribution in hexanes, toluene, methanol, water, 3:3:4:2. Methanol can be removed from the lower phase by concentration in vacuo, resulting in an aqueous solution containing the antibiotic activity. The mixture of antibiotics can be extracted into ethyl acetate and then purified by countercurrent chromatography in hexanes, ethyl acetate, methanol, water, 1:1:1:1. During the course of this procedure, aerocyanidin is separated from aerocavin. The fractions containing each of the antibiotics can be pooled. The fractions containing aerocyanidin can be further purified by reverse-phase chromatography on a macroporous styrene-divinylbenzene polymer with a linear gradient of acetonitrile in water. Extraction of the combined active fractions with ethyl acetate followed by concentration in vacuo gives aerocyanidin as a colorless crystalline solid. The fractions containing aerocavin can be purified as described above.

Aerocavin and aerocyanidin are acidic substances that form salts with various organic and inorganic bases. Pharmaceutically acceptable salts are preferred, although other salts are also useful, e.g., in the isolation of the antibiotics. Salts of the antibiotics form an integral part of this invention and are readily prepared using art-recognized techniques. Exemplary salts include ammonium salts, alkali metal salts (e.g., sodium and potassium salts), alkaline earth metal salts (e.g., calcium and magnesium salts) and other salts with organic bases such as dicyclohexylamine, benzathine, hydrabamine and N-methyl-D-glucamine.

The following examples further illustrate the preparation of aerocavin and aerocyanidin.

EXAMPLE 1

Preparation of Aerocavin

Yeast extract, glucose, soil extract, salts, agar slants were seeded with *Aeromonas caviae*, A.T.C.C. No. 53434, incubated overnight at 25° C. and used to inoculate 100 ml portions of an aqueous medium contained in 500 ml Erlenmeyer flasks. The composition of the germination medium was:

| Yeast extract | 4.0 g |
|---|---|
| Malt extract | 10.0 g |
| Dextrose | 4.0 g |
| Distilled water to | 1000 ml |

The medium, adjusted to pH 7.3, was sterilized at 121° C. and at 15 lbs. steam pressure for 15 minutes prior to use. The inoculated germination flasks were incubated at 25° C for approximately 24 hours on a rotary shaker, operating at 300 rpm with a 2 inch stroke.

A 1% (v/v) transfer was made from the germination flasks to 100 ml portions of a medium of the following composition contained in 500 ml Erlenmeyer flasks:

| Yeast extract | 10.0 g |
|---|---|
| Malt extract | 10.0 g |
| Peptone | 1.0 g |
| Dextrose | 20.0 g |
| Distilled water to | 1000 ml |

The medium, adjusted to pH 7, was sterilized at 121° C. and at 25 lbs. steam pressure for 15 minutes prior to use. The inoculated flasks were incubated at 25° C. for about 24 hours on a rotary shaker operating at 300 rpm with a 2 inch stroke.

The contents of the flasks were pooled and the pooled broth centrifuged, yielding approximately 160 liters of broth supernate, pH 6.6. The supernate, adjusted to pH 5.5 with 6N hydrochloric acid, was extracted with two 80 liter portions of ethyl acetate. The extracts were pooled and then concentrated in vacuo at a temperature equal to or less than 40° C. to yield 14.6 grams of a syrup.

The 14.6 grams of syrup was charged onto a silicic acid column (2.5 cm×54 cm) packed in hexane:-chloroform, 1:1 (v/v). Elution of the column was begun with 500 ml of hexane:chloroform, 1:1 (v/v) and followed by elution with 500 ml of hexane:chloroform, 1:2 (v/v), 3 liters of chloroform and finally with 500 ml of chloroform: methanol, 99:1 (v/v). The active fractions were collected, pooled and concentrated in vacuo giving 4 g of residue. This residue, dissolved in 20 ml of a solvent consisting of methanol:chloroform: heptane, 1:3:6 (v/v/v) was then chromatographed on a Sephadex LH-20 column (2.5 cm×50 cm) packed in the same solvent. This same solvent was used to elute the bioactive material, which was collected and concentrated in vacuo giving a residue of 1.1 g. The residue, dissolved in 20 ml of heptane, was placed onto a cellulose column (Whatman CF 11, 2.5 cm×28 cm) packed in heptane. The column was eluted with 500 ml portions of heptane followed by heptane:ether, 1:1 (v/v). The concentrate of the pooled, active fractions was rechromatographed on a cellulose column (Whatman CF11, 2.5 cm×25 cm) packed in petroleum ether (35°–60° C.). Elution of the column with 500 ml portions of petroleum ether, petroleum ether: heptane, 1:1 (v/v), heptane, heptane:ether, 1:1 (v/v), and finally ether resulted in the activity being recovered. The pooled, active fractions were concentrated in vacuo, and the residue 0.2 g, was dissolved in a small volume of heptane:ethyl acetate, 9:1 (v/v), from which crystalline aerocavin (100 mg) was obtained.

Aerocavin was found to be a colorless acidic substance with empirical formula $C_{27}H_{44}O_6$, MW 464 (high resolution FAB mass spectometry) and melting point of 127° C.; UV max in MeOH 220nm ($E_1$ $_{cm}^{1\%}$ 250); $[\alpha]_D^{22} = +25.1°$ (c=0.9, methanol; $^1$H NMR (CDCl$_3$) ϵ0.87 (3H, t, J=6.8 Hz), 1.26 (ca. 13H), 1.45 (ca. 3H, m), 1.49 (3H, s), 1.60 (1H, ddd, J=2.6, 8.6, 14.6 Hz), 1.88 (2H, m), 2.02 (1H, dd, J=11.7, 11.7 Hz), 2.22 (1H, dd, J=3.4, 12.0 Hz), 2.25 (1H, d, J=11.3 Hz), 2.50 (2H, m), 2.58 (1H, ddd, J=4.4, 13.2, ca. 18.4 Hz), 3.13 (1H, d, J=15.2 Hz), 3.20 (1H, d, J=15.2 Hz), 3.66 (1H, m), 3.88 (1H, m), 4.01 (1H, dd, J=8.5, 13.2 Hz), 5.11 (1H, m), 5.26 (1H, m), 5.26 (1H, ddd, J=4.7, 8.0, 17.0 Hz), 5.37 (1H, ddd, J=5.2, 8.7, 14.0 Hz), 5.76 (1H, s), 6.02 ppm (2 to 3H, broad s); $^{13}$C NMR (CDCl$_3$)ϵ 14.0, 16.4, 22.6, 25.4, 29.2, 29.5 (3C), 30.9, 31.8, 34.6, 37.1, 38.4, 39.5, 44.8, 49.4, 65.6, 69.1, 70.9, 120.6, 124.9, 125.6, 129.2, 133.7, 152.1, 165.2, 174.0 ppm; IR (KBr) 3450, 3025, 2955, 2927, 2856, 1721, 1699, 1649, 1377, 1235, 1187, 1156, 1119, 1062, 965 cm$^{-1}$.

The antibiotic was substantially soluble in methanol, acetone, ethyl acetate, less soluble in heptane and insoluble in water.

Biological Activity of Aerocavin

The minimum inhibitory concentration (MIC) of aerocavin was determined by an agar dilution technique. The test organisms were prepared from frozen stocks and diluted to give a final level of $10^7$ CFU/ml (CFU is colony forming units). Aerocavin was dissolved in the appropriate diluent at a concentration of 1,000 μg/ml. Two fold dilutions were made in Yeast Beef Broth (Difco), resulting in a range from 1,000 μg/ml to 0.5 μg/ml. A 1.5 ml sample of each dilution was placed into individual petri dishes to which 13.5 ml of K-10 agar* was added. The final drug concentration in the agar ranged from 100 μg/ml to 0.05 μg/ml. Organism growth control plates containing agar only were prepared and inoculated before and after the test plates. The organisms were applied to the surface of each plate with the Denley Multipoint Inoculator (which delivers approximately 0.001 ml of each organism) resulting in a final inoculum level of $10^4$ CFU on the agar surface.
*K-10 agar Beef extract: 1.5 g; Yeast extract: 3.0 g; Peptone: 6.0 g; Dextrose: 1.0 g; Agar: 15.0 g; Distilled water to: 1000 ml.

The plates were incubated at 37° C. for 18 hours and the MIC's then determined. The MIC is the lowest concentration of compound inhibiting growth of the organism.

The results of the agar dilution assays are:

| Organism | SC No.* | MIC(μg/ml) |
|---|---|---|
| Staphylococcus aureus | 1276 | 6.3 |
| Staphylococcus aureus | 2399 | 6.3 |
| Staphylococcus aureus (Tetracycline$^R$)** | 10016 | 3.1 |
| Staphylococcus aureus (Penicillin$^R$) | 9593 | 6.3 |
| Staphylococcus aureus (Erythromycin$^R$) | 10820 | 3.1 |
| Staphylococcus epidermidis | 9052 | 6.3 |
| Staphylococcus epidermidis (Penicillin$^R$) | 10547 | 3.1 |
| Escherichia coli | 8294 | 100.0 |
| Escherichia coli | 10857 | 12.5 |
| Pseudomonas aeruginosa | 9545 | 25.0 |
| Acinetobacter calcoaceticus | 8333 | 12.5 |

*SC No. is the number in the microorganism collection of E. R. Squibb & Sons, Inc., Princeton, New Jersey.
**($^R$) indicates that the organism is resistant to the antibiotic named.

EXAMPLE 2

Preparation of Aerocyanidin

Agar slants composed of the following:

| | |
|---|---|
| Yeast extract | 5.0 g |
| Glucose | 5.0 g |
| MgSO$_4$.7H$_2$O | 0.1 g |
| FeSO$_4$.7H$_2$O | 0.1 g |
| Soil extract filtrate* | 200.0 ml |
| Agar | 17.5 g |
| Tap water | 800.0 ml |

*Soil extract filtrate is made by bringing to a boil a suspension of soil in tap water (1:2, v/v) and then allowing to simmer for about 60 minutes. After cooling, the extract is filtered through cheesecloth, then centrifuged to remove most of the remaining solids and finally filtered through Whatman 4 filter paper. The resulting liquid is sterilized by autoclaving at 121° C. for 20 minutes.

were seeded with Aeromonas caviae A.T.C.C. No. 53434, incubated overnight at 25° C. and used to inoculate 100 ml portions of an aqueous medium contained in 500 ml Erlenmeyer flasks. The composition of the medium was:

| | |
|---|---|
| Tryptone | 5.0 g |
| Malt extract | 3.0 g |
| Glucose | 10.0 g |
| Yeast extract | 3.0 g |
| Distilled water to | 1000 ml |

The medium was sterilized at 121° C. and at 15 lbs. steam pressure for 15 minutes prior to use.

The inoculated flasks were incubated at 25° C. for about 24 hours on a rotary shaker operating at 300 rpm with a 2 inch stroke. Growth from these flasks was then used to inoculate 100 ml portions of fresh medium of the same composition contained in 500 ml Erlenmeyer flasks. These flasks were also incubated at 25° C. on a rotary shaker with the same conditions as just described for the preceding stage. This growth was then used as the source of inoculum (1.5%, v/v) for 250 liters of medium in a 300 liter stainless steel vessel. The medium had the following compositions:

| | |
|---|---|
| Tryptone | 5.0 g |
| Malt extract | 3.0 g |

| | |
|---|---|
| Cerelose hydrate | 11.0 g |
| Ucon LB 625 | 0.5 ml |
| Distilled water to | 1000 ml |

The medium was sterilized at 121° C. and at 15 lbs. steam pressure for 30 minutes prior to use.

The fermentation proceeded for 24 hours at 25° C., with an agitation rate of 130 rpm, an airflow of 10 CFM and a pressure of 10 psig. At the completion of the fermentation, the broth was harvested. The pH was adjusted to 6 by the addition of 3 M phosphoric acid, chilled to 11° C. and centrifuged to remove cells and other particulate matter. The clear supernate was placed directly into a vessel containing ethyl acetate, 125 liters, while stirring. The organic and aqueous phases were separated by centrifugation and the clear supernate, 58 liters, was concentrated in vacuo at $\leq 20°$ C. to 2 liters. Solids that formed during the concentration were removed by filtration. The clear filtrate was then washed with 2 liters of sodium 0.1 M phosphate buffer, pH 6.0, followed by three 800 ml portions of water. The ethyl acetate layer, 1.6 liters, was concentrated in vacuo to give a residue, 87 g, that was subjected to a 2 funnel, 3 transfer countercurrent distribution in hexanes, toluene, methanol, water, 3:3:4:2, v/v/v/v, 850 ml per phase, with the lower phase being the mobile phase. After completion of the distribution, the lower phases were pooled and methanol removed by concentration in vacuo. The resulting aqueous solution was extracted with ethyl acetate, 350 ml, and the organic phase separated and then concentrated in vacuo to give a residue, 4.1 grams. The residue was dissolved in 10 ml each of the upper and lower phases of a partition system composed of hexanes, ethyl acetate, methanol, water, 1:1:1:1, v/v/v/v, and chromatographed in this solvent system on a high-speed countercurrent chromatograph (P.C. Inc., Potomac, Md.) operated at 800 rpm using a multilayer teflon tubing (1.6 mm, i.d.) coil with a volume of 330 ml. The system was eluted with the upper phase at 4 ml per minute. Aerocyanidin emerged between 250 and 370 ml. The fractions containing aerocyanidin were combined, washed with an equal volume of water, and the aqueous phase back-washed with ethyl acetate. The organic solvent pool, 250 ml, was concentrated in vacuo to a residue, 669 mg. The residue was mixed with 10 ml of acetonitrile: water, 3:7, v/v, and the resulting turbid mixture was placed onto a 2.5×20 cm column of MCI GEL CHP20P resin* packed in acetonitrile:water, 3:7, v/v. The column was eluted at 2 ml per minute with a linear gradient ranging from 30 to 70% acetonitrile in water over a volumn of 2.2 liters. Aerocyanidin eluted between 700 and 760 ml.

The active fractions were pooled and the pool was diluted with water, 60 ml. The diluted pool was extracted twice with ethyl acetate. The two ethyl acetate extracts were combined and the pool washed twice with water. The resulting ethyl acetate solution, 170 ml, contained 138.4 mg of aerocyanidin. Aerocyanidin was stored in this solution at 4° C. since the antibiotic is less stable in the solid state. A small sample, when concentrated to dryness in a nitrogen stream, gave a crystalline residue that melted at 59° to 62° C. The highest melting point observed for material obtained by the above procedure was 63.5° to 65.5° C.

Aerocyanidin was found to be a colorless, acidic substance, $[\alpha]_D^{23} = -20°$ (c=0.5, methanol), $^1$H NMR (CDCL$_3$)$\delta$1.2 to 1.75 (16H), 1.76 (3H, s), 2.34 (2H, t, J=7.3, 7.3 Hz), 2.84 (1H, d, J=8.1 Hz), 3.66 (1H, td, J=8.0, 8.0, 4.5 Hz), ca. 6.8 ppm (2H, broad); $^{13}$C NMR (CDCL$_3$) $\delta$22.1, 24.6, 24.6, 29.0, 29.1, 29.2, 29.3, 29.3, 34.0, 34.6, 64.8, 65.2 (broad), 69.6, 161.0, 179.6 ppm; IR (KBr) 2971, 2934, 2916, 2853, 2142, 1712, 1114, 1086, 886, 810 cm$^{-1}$; mass spectrum (FAB) 284.1866 [calc'd for C$_{15}$H$_{26}$NO$_4$ (M+H$^+$): 284.1862], UV (methanol) end absorption.

Biological Activity of Aerocyanidin

Using the methodology described for the determination of the biological activity of aerocavin, the biological activity of aerocyanidin was determined. The results of the agar dilution assays are:

| Organism | SC No. | MIC(μg/ml) |
|---|---|---|
| Staphylococcus aureus | 1276 | <0.05 |
| Staphylococcus aureus | 2399 | <0.05 |
| Staphylococcus aureus | 2400 | <0.05 |
| Streptococcus faecalis | 9011 | 0.2 |
| Streptococcus agalactiae | 9287 | <0.05 |
| Micrococcus luteus | 2495 | 0.4 |
| Escherichia coli | 8294 | >50.0 |
| Escherichia coli | 10896 | 25.0 |
| Escherichia coli | 10909 | 1.6 |
| Klebsiella aerogenes | 10440 | >50.0 |
| Klebsiella pneumoniae | 9527 | >50.0 |
| Proteus mirabilis | 3855 | 1.6 |
| Salmonella typhosa | 1195 | 25.0 |
| Shigella sonnei | 8449 | 25.0 |
| Enterobacter cloacae | 8236 | 50.0 |
| Pseudomonas aeruginosa | 8329 | >50.0 |

What is claimed is:

1. The compound [3E,6E,9E,12α, 14β(R*)]-12-hydroxy-14-(2-hydroxyundecyl)-10-methyl-2-oxooxacyclotetradeca-3,6,9-triene-4-acetic acid having an optical rotation of about [α $_D^{22}$ = +25.1° (c=0.9, methanol), or a pharmaceutically acceptable salt thereof.

* * * * *